(12) United States Patent
Mostafavi

(10) Patent No.: US 6,621,889 B1
(45) Date of Patent: Sep. 16, 2003

(54) METHOD AND SYSTEM FOR PREDICTIVE PHYSIOLOGICAL GATING OF RADIATION THERAPY

(75) Inventor: Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 4 days.

(21) Appl. No.: 09/178,383

(22) Filed: Oct. 23, 1998

(51) Int. Cl.$^7$ ................................................. A61N 5/10
(52) U.S. Cl. ........................................... 378/65; 378/95
(58) Field of Search ..................................... 378/95, 65

(56) References Cited

U.S. PATENT DOCUMENTS

| | | | |
|---|---|---|---|
| 3,861,807 A | 1/1975 | Lescrenier | 356/152 |
| 3,871,360 A | 3/1975 | Van Horn et al. | 128/2.05 R |
| 3,952,201 A | * 4/1976 | Hounsfield | 378/8 |
| 4,031,884 A | 6/1977 | Henzel | 128/2.05 R |
| 4,262,306 A | 4/1981 | Renner | 358/93 |
| 4,463,425 A | 7/1984 | Hirano et al. | 364/417 |
| 4,994,965 A | 2/1991 | Crawford et al. | 364/413.15 |
| 5,080,100 A | 1/1992 | Trotel | 128/653.1 |
| 5,271,055 A | * 12/1993 | Hsieh | 378/95 |
| 5,279,309 A | 1/1994 | Taylor et al. | 128/782 |
| 5,295,483 A | 3/1994 | Nowacki et al. | 128/660.03 |
| 5,315,630 A | 5/1994 | Sturm et al. | 378/65 |
| 5,389,101 A | 2/1995 | Heilbrun et al. | |
| 5,394,875 A | 3/1995 | Lewis et al. | 128/660.09 |
| 5,446,548 A | 8/1995 | Gerig et al. | 356/375 |
| 5,538,494 A | 7/1996 | Matsuda | 600/1 |
| 5,603,318 A | 2/1997 | Heilbrun et al. | |
| 5,727,554 A | 3/1998 | Kalend et al. | 128/653.1 |
| 5,764,723 A | * 6/1998 | Weinberger | 378/95 |
| 5,784,431 A | 7/1998 | Kalend et al. | |
| 5,823,192 A | 10/1998 | Kalend et al. | |
| 5,836,954 A | 11/1998 | Heilbrun et al. | |
| 6,138,302 A | 10/2000 | Sashin et al. | |
| 6,146,390 A | 11/2000 | Heilbrun et al. | |
| 6,165,181 A | 12/2000 | Heilbrun et al. | |
| 6,185,445 B1 | 2/2001 | Knüttel | 600/411 |
| 6,185,446 B1 | 2/2001 | Carlsen, Jr. | 600/411 |
| 6,198,959 B1 | 3/2001 | Wang | 600/413 |

FOREIGN PATENT DOCUMENTS

| | | | |
|---|---|---|---|
| FI | 79458 | 1/1919 | |
| WO | WO 98/16151 | 4/1998 | A61B/5/0205 |

OTHER PUBLICATIONS

Ference A. Jolesz; "Image–Guided Procedures and the Operating Room of the Future"; Radiology; SPL Technical Report # 48; May 1997; 204; 601–612.

J.M. Balter et al.; "Uncertainties In CT–Based Radiation Therapy Treatment Planning Associated With Patient Breathing"; *Int. J. Radiat. Oncol., Biol., Phys.* 36; pp. 167–174 (Aug. 1996).

S.C. Davies et al.; "Ultrasound Quantitation Of Respiratory Organ Motion in The Upper Abdomen"; *Br. J. Radiol.* 67; pp. 1096–1102 (Nov. 1994).

R.L. Ehman et al.; Magnetic Resonance Imaging With Respiratory Gating: Techniques and Advantages; *Am. J. Roentgenol* 143; pp. 1175–1182 (Dec. 1984).

H. Frölich et al.; "A Simple Device For Breath–Level Monitoring During CT"; *Radiology* 156; p. 235 (Jul. 1985).

(List continued on next page.)

*Primary Examiner*—Craig E. Church
(74) *Attorney, Agent, or Firm*—Bingham McCutchen LLP

(57) ABSTRACT

A method and system for physiological gating for radiation therapy is disclosed. A method and system for detecting and predictably estimating regular cycles of physiological activity or movements is disclosed. Another disclosed aspect of the invention is directed to predictive actuation of gating system components. Yet another disclosed aspect of the invention is directed to physiological gating of radiation treatment based upon the phase of the physiological activity.

28 Claims, 10 Drawing Sheets

OTHER PUBLICATIONS

R.M. Henkelman et al.; "How Important Is Breathing In Radiation Therapy Of The Thorax?"; *Int. J. Radiat. Oncol., Biol., Phys.* 8; pp. 2005–2010 (Nov. 1982).

M.B.M. Hofman et al.; "MRI Of Coronary Arteries: 2D Breath–Hold vs. 3D Respiratory–Gated Acquisition"; *J. of Comp. Assisted Tomography* 19; pp. 56–62 (Jan./Feb. 1995).

G.J. Kutcher et al.; "Control, Correction, and Modeling Of Setup Errors and Organ Motion", *Semin. Radiat. Oncol.* 5; pp. 134–145 (Apr. 1995).

H.W. Korin et al.; "Respiratory Kinematics Of The Upper Abdominal Organs: A Quantitative Study"; *Magn. Reson. Med.* 23; pp. 172–178 (Jan. 1992).

H.D. Kubo et al.; "Respiration Gated Radiotherapy Treatment: A Technical Study"; *Phys. Med. Biol.* 41; pp. 83–91; (1996).

C.E. Lewis et al.; "Comparison Of Respiratory Triggering And Gating Techniques For The Removal Of Respiratory Artifacts In MR Imaging"; *Radiology* 160; pp. 803–810; (Sep. 1986).

D. Li et al.; "Coronary Arteries: Three–Dimensional MR Imaging With Retrospective Respiratory Gating"; *Radiology* 201; pp. 857–863 (Dec. 1996).

M.A. Moerland et al.; "The Influence Of Respiration Induced Motion Of The Kidneys On The Accuracy Of Radiotherapy Treatment Planning, A Magnetic Resonance Imaging Study", *Radiotherapy Oncol.* 30, pp. 150–154 (1994).

K. Ohara et al.; "Irradiation Synchronized With Respiration Gate"; *Int. J. Radiat. Oncol., Biol. Phys.* 17; pp. 853–857; (Oct. 1989).

J.N. Oshinski et al.; "Two–Dimensional Coronary MR Angiography Without Breath Holding"; *Radiology* 201; pp. 737–743; (Dec. 1996).

C.J. Ritchie et al.; "Predictive Respiratory Gating: A New Method To Reduce Motion Artifacts On CT Scans"; *Radiology* 190; pp. 847–852; (Mar. 1994).

C.S. Ross et al.; "Analysis Of Movement Of Intrathoracic Neoplasms Using Ultrafast Computerized Tomography"; *Int. J. Radiat. Oncol., Biol., Phys.* 18; pp. 671–677; (Mar. 1990).

V.M. Runge et al.; "Respiratory Gating In Magnetic Resonance Imaging at 0.5 Tesla"; *Radiology* 151; pp. 521–523; (May 1984).

T.S. Sachs et al.; "Real–Time Motion Detection In Spiral MRI Using Navigators", *Magn. Reson. Med.* 32; pp. 639–645; (Nov. 1994).

L.H. Schwartz et al.; "Kidney Mobility During Respiration"; *Radiother. Oncol.* 32; pp. 84–86; (1994).

M. Paivansalo Suramo et al.; "Cranio–caudal Movements Of The Liver, Pancreas And Kidneys In Respiration", *Acta Radiol. Diagn.* 2; pp. 129–131; (1984).

Peltola, Seppo M.Sc.; "Gated Radiotherapy To Compensate For Patient Breathing"; *Proceedings of the Eleventh Varian Users Meeting*; Marco Island, Florida; May 11–13, 1986.

Mah, Katherine, et al.; "Time Varying Dose Due To Respiratory Motion During Radiation Therapy Of The Thorax"; $8^{th}$ *Int'l Conference on the Use of Computers In Radiation Therapy*; Toronto, Canada; Jul. 9–12, 1984; pp. 294–298.

Mori, Masayuki, et al.; "Accurate Contiguous Sections Without Breath–Holding On Chest CT.."; *AJR:162*, May 1994; pp. 1057–1062.

Robinson, Terry E., et al.; "Standardized High–Resolutiono CT of the Lung Using A Spriometer–Triggered Electron Beam CT Scanner"; *AJR:172*; Jun. 1999; pp. 1636–1638.

Luker, Gary D., et al.; "Ghosting of Pulmonary Nodules With Respiratory Motion . . . ", *AJR:167*; Nov. 1996; pp. 1189–1193.

Li, Debiao, et al.; "Coronary Arteries: Three–dimentional MR Imaging With Retrospective Respiratory Gating"; *Radiology*; Dec. 1996; pp. 857–863; vol. 201; No. 3.

Kacheiriess, Marc, et al.; "Electrocardiogram–correlated Image Reconstruction From Subsecond Spiral Computed Tomography Scans Of The Heart"; *Med. Phys.25(12)*; Dec. 1998; pp. 2417–2431.

Tada, Takuhito, et al.; "Lung Cancer: Intermittent Irradiation Synchronized With Respiratory Motion–Results of a Pilot Study"; *Radiology*; Jun., 1998; pp. 779–783; vol. 207; No. 3.

Solberg, Timothy D., et al.; "Feasibility of Gated IMRT".

Wong, John W., et al.; "The Use Of Active Breathing Control (ABC) To Reduce Margin For Breathing Motion"; *Int. J. Radiation Oncology Biol. Phys.*; 1999; pp. 911–919; vol. 44; No. 4.

Mageras, Gig, et al.; "Initial Clinical Evaluation Of A Respiratory Gating Radiotherapy System"; *Dept. of Medical Physics, Memorial Sloan–Kettering Cancer Center..*

Yorke, Ellen, et al.; "Respiratory Gating Of Sliding Window IMRT".

Keatley, Eric, et al.; "Computer Automated Diaphragm Motion Quantification in a Fluoroscopic Movie"; *Dept. of Medical Physics, Memorial Sloan–Kettering Cancer Center.*

Kubo, H. Dale, et al.; "Breathing–Synchronized Radiotherapy Program at the University of California Davis Cancer Center"; *Med. Phys. 27(2)*; Feb. 2000; pp. 346–353.

Iwasawa, Tae, et al.; "Normal In–Plane Respiratory Motion of the Bilateral Hemidiaphragms Evaluated By Sequentially Subtracted Fast Magnetic Resonance Images"; *Journal of Thoracic Imaging*; 1999; pp. 130–134; vol. 14; No. 2.

Kim, W.S., et al.; "Extraction of Cardiac and Respiratory Motion Cycles by Use of Projection Data and Its Applications to NMR Imaging"; *Magnetic Resonance in Medicine 13*; 1990; pp. 25–37.

Woodard, Pamela K., et al.; "Detection of Coronary Stenoses on Source and Projection Images Using Three–Dimensional MR Angiography With Retrospective Respiratory Gating: Preliminary Experience"; *AJR:170*; Apr. 1998; pp. 883–888.

Sinkus, Ralph, et al.; "Motion Pattern Adapted Real–Time Respiratory Gating"; *Magnetic Resonance in Medicine 41*; 1999; pp. 148–155.

Weiger, Markus, et al.; "Motion–Adapted Gating Based on k–Space Weighting For Reduction of Respiratory Motion Artifacts"; *Magnetic Resonance in Medicine 38*; 1997; pp. 322–333.

Wang, Yi, et al.; "Implications For The Spatial Resolution in Coronary Imaging"; *Magnetic Resonance in Medicine 33*; 1995; pp. 713–719.

Ritchie, Cameron J., et al.; "Predictive Respiratory Gating: A New Method To Reduce Motion Artifacts on CT Scans"; *Radiology*; 1994; pp. 847–852; vol. 190; No. 3.

Kubo, H. Dale, et al.; "Potential and Role of a Prototype Amorphous Silicon Array Electronic Portal Imaging Device in Breathing Synchronized Radiotherapy"; *Med. Phys. 26(11)*; Nov. 1999; pp. 2410–2414.

Article by Hideo D. Kubo & Bruce C. Hill entitled "Respiration Gated Radiotherapy Treatment: A Technical Study", published in *Physics In Medicine & Biology*, Jan. 1996, No. 1, pp. 83–91.

\* cited by examiner

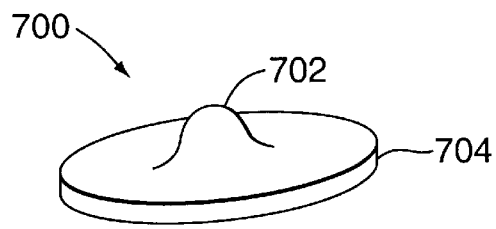
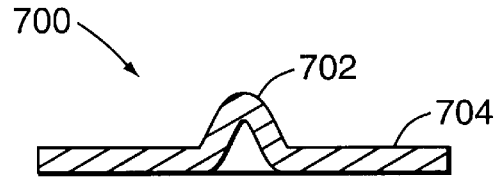
FIG. 7a   FIG. 7b
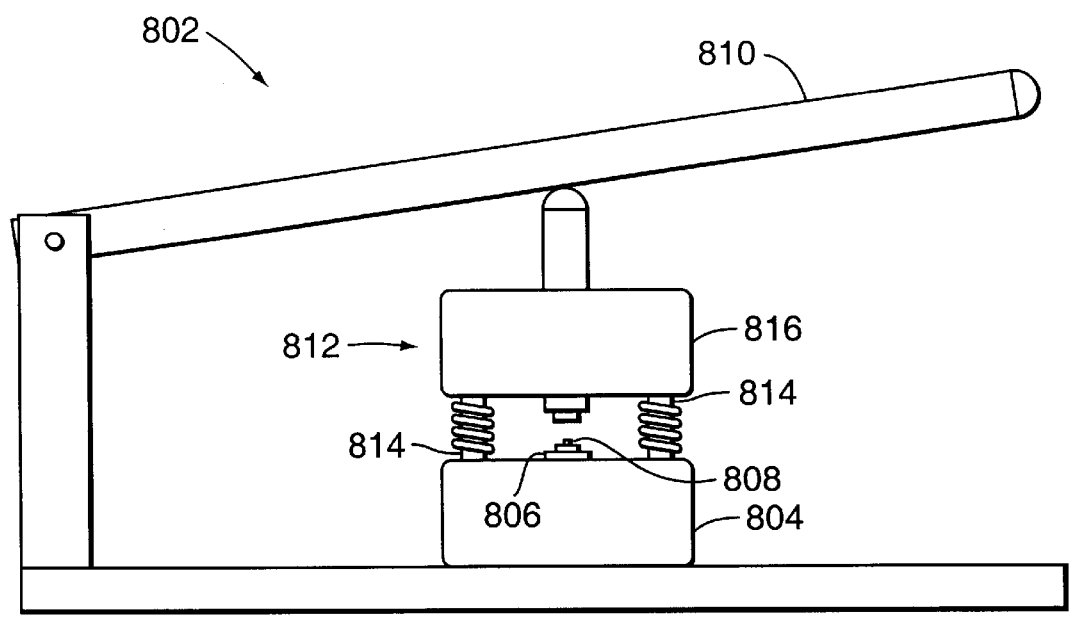
FIG. 8

METHOD AND SYSTEM FOR PREDICTIVE PHYSIOLOGICAL GATING OF RADIATION THERAPY

BACKGROUND OF THE INVENTION

1. Field of the Invention

The present invention relates to medical methods and systems. More particularly, the invention relates to a method and system for physiological gating of radiation therapy.

2. Background

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. In certain types of radiotherapy, the irradiation volume can be restricted to the size and shape of the tumor or targeted tissue region to avoid inflicting unnecessary radiation damage to healthy tissue. For example, conformal therapy is a radiotherapy technique that is often employed to optimize dose distribution by conforming the treatment volume more closely to the targeted tumor.

Normal physiological movement represents a limitation in the clinical planning and delivery of conventional radiotherapy and conformal therapy. Normal physiological movement, such as respiration or heart movement, can cause a positional movement of the tumor or tissue region undergoing irradiation. If the radiation beam has been shaped to conform the treatment volume to the exact dimensions of a tumor, then movement of that tumor during treatment could result in the radiation beam not being sufficiently sized or shaped to fully cover the targeted tumoral tissue.

One approach to this problem involves physiological gating of the radiation beam during treatment, with the gating signal synchronized to the movement of the patient's body. In this approach, instruments are utilized to measure the physiological state and/or movement of the patient. For example, respiration has been shown to cause movements in the position of a lung tumor in a patient's body. If radiotherapy is being applied to the lung tumor, then a temperature sensor, strain gauge, preumotactrograph, or optical imaging system can be utilized to measure the patient's respiration cycle. These instruments can produce a signal indicative of the movement of the patient during the respiratory cycle. The radiation beam can be gated based upon certain threshold amplitude levels of the measured respiratory signal, such that the radiation beam is disengaged or stopped during particular time points in the respiration signal that correspond to excessive movement of the lung tumor.

Known approaches to physiological gating of radiation therapy are reactive, that is, known approaches utilize gating methods that slavishly react to measured levels of physiological movements. One drawback to reactive gating systems is that the measured physiological movement may involve motion that that is relatively fast when compared to the effectively operating speeds of gating system components. Thus, a purely reactive gating system may not be able to react fast enough to effectively gate the applied radiation. For example, the gating system may include a switch for gating the radiation treatment, in which the switch requires a given time period Δt to fully engage. If the switching time period Δt is relatively slow compared to the measured physiological motion cycle, then a system employing such a switch in a reactive manner may not be able to effectively gate the application of radiation at appropriate time points during the radiation therapy.

Therefore, there is a need for a system and method to address these and other problems of the related art. There is a need for a method and system for physiological gating which is not purely reactive to measure physiological movement signals.

SUMMARY OF THE INVENTION

The present invention provides an improved method and system for physiological gating for radiation therapy. According to an aspect, the invention comprises a method and system for detecting and predictably estimating regular cycles of physiological activity or movements. Another aspect of the invention is directed to predictive actuation of gating system components. Yet another aspect of the invention is directed to physiological gating of radiation treatment based upon the phase of the physiological activity.

These and other aspects, objects, and advantages of the invention are described below in the detailed description, drawings, and claims.

BRIEF DESCRIPTION OF THE DRAWINGS

The accompanying drawings are included to provide a further understanding of the invention and, together with the Detailed Description, serve to explain the principles of the invention.

FIG. 6b depicts a front view of the camera of FIG. 6a.

FIG. 7a depicts a retro-reflective marker according to an embodiment of the invention.

FIG. 7b depicts a cross-sectional view of the retro-reflective marker of FIG. 7a.

FIG. 8 depicts an apparatus for making a retro-reflective marker.

DETAILED DESCRIPTION

An aspect of the present invention comprises a method for detecting and predictively estimating regular cycles of physiological activity or movement. The method of the invention can be employed for any regular physiological activity, including, for example, the respiratory or cardiac cycles.

In operation, one or more sets of data representative of the physiological activity of interest are collected for the patient. For example, an electrocardiograph can be employed to generate data representative of the cardiac cycle. To generate data representative of the respiration cycle, a temperature sensor, strain gauge or preumotactrograph can be employed. Other instruments or mechanisms can be employed within the scope of the invention to obtain sets of data representative of physiological activity or movements.

Figure 1:
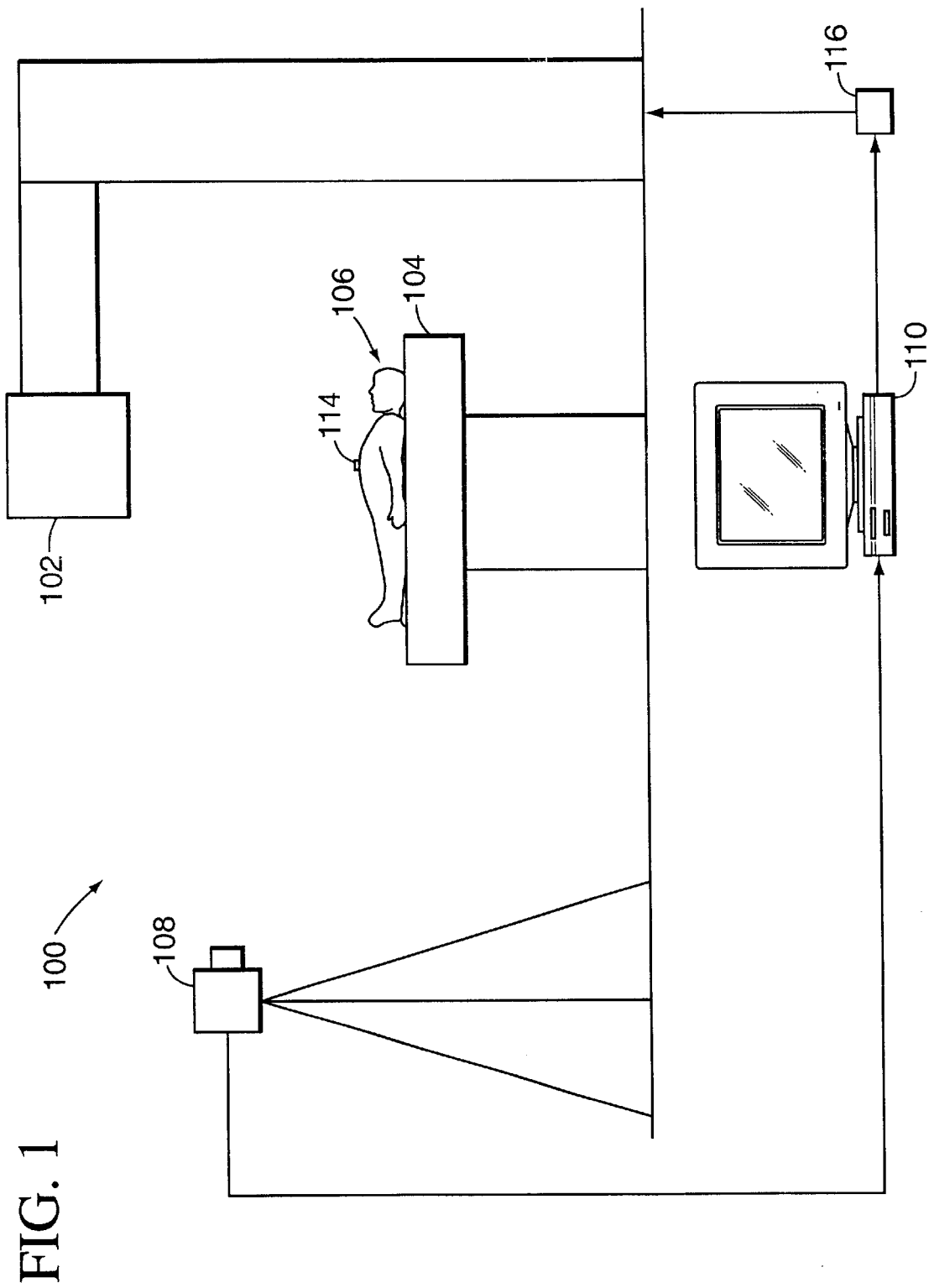
FIG. 1 depicts the components of a system for physiological gating according to an embodiment of the invention.

FIG. 1 depicts the components of an embodiment of a system 100 for physiological gating of radiation therapy, in which data representative of physiological activity is collected with an optical imaging apparatus. System 100 comprises a radiation beam source 102 (such as a conventional linear accelerator) which is positionally configured to direct a radiation beam at a patient 106 located on treatment table 104. A switch 116 is operatively coupled to the radiation beam source 102. Switch 116 can be operated to suspend the application of the radiation beam at patient 106. In an embodiment, switch 116 is part of the mechanical and electrical structure of radiation beam source 102. Alternatively, switch 116 comprises an external apparatus that is connected to the control electronics of radiation beam source 102.

An optical or video image apparatus, such as video camera 108, is aimed such that as least part of the patient 106 is within the camera's field of view. Camera 108 monitors patient 106 for motion relating to the particular physiological activity being measured. For example, if respiration movements of the patient is being monitored, then camera 108 can be configured to monitor the motion of the patient's chest. According to an embodiment, camera 108 is placed with its axis at approximately 45 degrees to the longitudinal axis of the patient 106. For measurement of respiration activity that could result in about 3–5 mm of chest motion, the video image field of view is preferably set to view an approximately 20 cm by 20 cm area of the patient's chest. For purposes of illustration only, a single camera 108 is shown in FIG. 1. However, the number of cameras 108 employed in the present invention can exceed that number, and the exact number to be used in the invention depends upon the particular application to which it is directed.

In an embodiment, one or more illumination sources (which are infrared sources in the preferred embodiment) project light at the patient 106 on treatment table 104. The generated light is reflected from one or more landmarks on the patient's body. The camera 108, which is directed at patient 106, captures and detects the reflected light from the one or more landmarks. The landmarks are selected based upon the physiological activity being studied. For example, for respiration measurements, landmarks are selected from one or more locations on the patient's chest.

The output signals of camera 108 are sent to a computer 110 or other type of processing unit having the capability to receive video images. According to a particular embodiment, computer 110 comprises an Intel Pentium-based processor running Microsoft Windows NT and includes a video frame grabber card having a separate channel for each video source utilized in the system. The images recorded by camera 108 are sent to computer 110 for processing. If camera 108 produces an analog output, the frame grabber converts the camera signals to a digital signal prior to processing by computer 110. Based upon the video signals received by computer 110, control signals can be sent from computer 110 to operate switch 116.

According to one embodiment, one or more passive markers 114 are located on the patient in the area to be detected for movement. Each marker 114 preferably comprises a reflective or retro-reflective material that can reflect light, whether in the visible or invisible wavelengths. If the illumination source is co-located with camera 108, then marker 114 preferably comprises a retro-reflective material that reflects light mostly in the direction of the illumination source. Alternatively, each marker 114 comprises its own light source. The marker 114 is used in place of or in conjunction with physical landmarks on the patient's body that is imaged by the camera 108 to detect patient movement. Markers 114 are preferably used instead of body landmarks because such markers 114 are easier to detect and track via the video image generated by camera 108. Because of the reflective or retro-reflective qualities of the preferred markers 114, the markers 114 inherently provide greater contrast in a video image to a light detecting apparatus such as camera 108, particularly when the camera 108 and illumination source are co-located.

Utilizing a video or optical based system to track patient movement provides several advantages. First, a video or optical based system provides a reliable mechanism for repeating measurement results between uses on a given patient. Second, the method of the invention is noninvasive, and even if markers are used, no cables or connections must be made to the patient. Moreover, if the use of markers is impractical, the system can still be utilized without markers by performing measurements of physiological activity keyed to selected body landmarks. Finally, the method of the invention is more accurate because it is based upon absolute measurement of external anatomical physical movement.

A possible inefficiency in tracking the markers 114 is that the marker may appear anywhere on the video frame, and all of the image elements of the video frame may have to be examined to determine the location of the marker 114. Thus, in an embodiment, the initial determination of locations for the marker 114 involves an examination of all of the image elements in the video frame. If the video frame comprise 640 by 480 image elements, then all 307200 (640*480) image elements are initially examined to find the location of the markers 114.

For real-time tracking of the marker 114, examining every image element for every video frame to determine the location of the marker 114 in real-time could consume a significant amount of system resources. Thus, in an embodiment, the real-time tracking of marker 114 can be facilitated by processing a small region of the video frame, referred to herein as a "tracking gate", that is placed based on estimation of the location of the already-identified marker 114 in the video frame. The previously determined location of a marker 114 defined in the previous video frame is used to define an initial search range (i.e., the tracking gate) for that same marker in real-time. The tracking gate is a relatively small portion of the video frame that is centered at the previous location of the marker 114. The tracking gate is expanded only if it does not contain the new location of the marker 114. As an example, consider the situation when the previously determined location of a particular marker is image element (50,50) in a video frame. If the tracking gate is limited to a 50 by 50 area of the video frame, then the tracking gate for this example would comprise the image elements bound within the area defined by the coordinates (25,50), (75,50), (50,25), and (50,75). The other portions of the video frame are searched only if the marker 106 is not found within this tracking gate.

Figure 2:
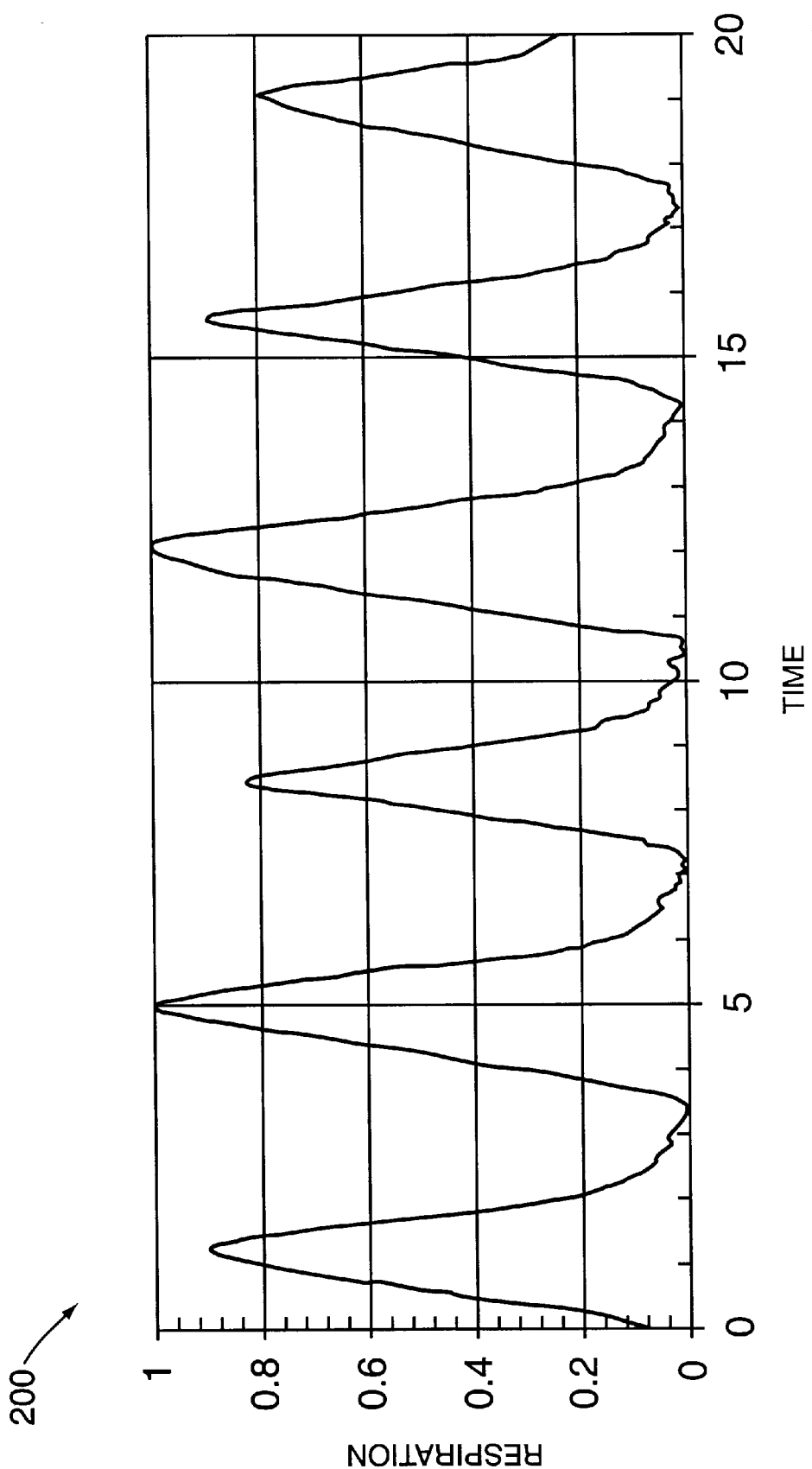
FIG. 2 depicts an example of a respiratory motion signal chart.

The video image signals sent from camera 108 to computer 110 are used to generate and track motion signals representative of the movement of marker 114 and/or landmark structures on the patient's body. FIG. 2 depicts an example of a motion signal chart 200 for respiratory movement that contains information regarding the movement of marker 114 during a given measurement period. The horizontal axis represents points in time and the vertical axis represents the relative location or movement of the marker 114. According to an embodiment, the illustrated signal in FIG. 2 comprises a plurality of discrete data points plotted along the motion signal chart 200.

An important aspect of physiological gating of radiotherapy is the determination of the boundaries of the "treatment intervals" for applying radiation. For gating purposes, threshold points can be defined over the amplitude range of the motion signal to determine the boundaries of the treatment intervals. Motion of the patient that fall outside the boundaries of the treatment intervals correspond to movement that is predicted to cause unacceptable levels of movement to the tumor or tissue targeted for irradiation. According to an embodiment, the treatment intervals correspond to the portion of the physiological cycle in which motion of the clinical target volume is minimized. Other factors for determining the boundaries of the treatment intervals include identifying the portion of the motion signals involving the least movement of the target volume or the portion of the motion signal involving the largest separation of the target volume from organs at risk. Thus, the radiation beam pattern can be shaped with the minimum possible margin to account for patient movement.

Figure 3:
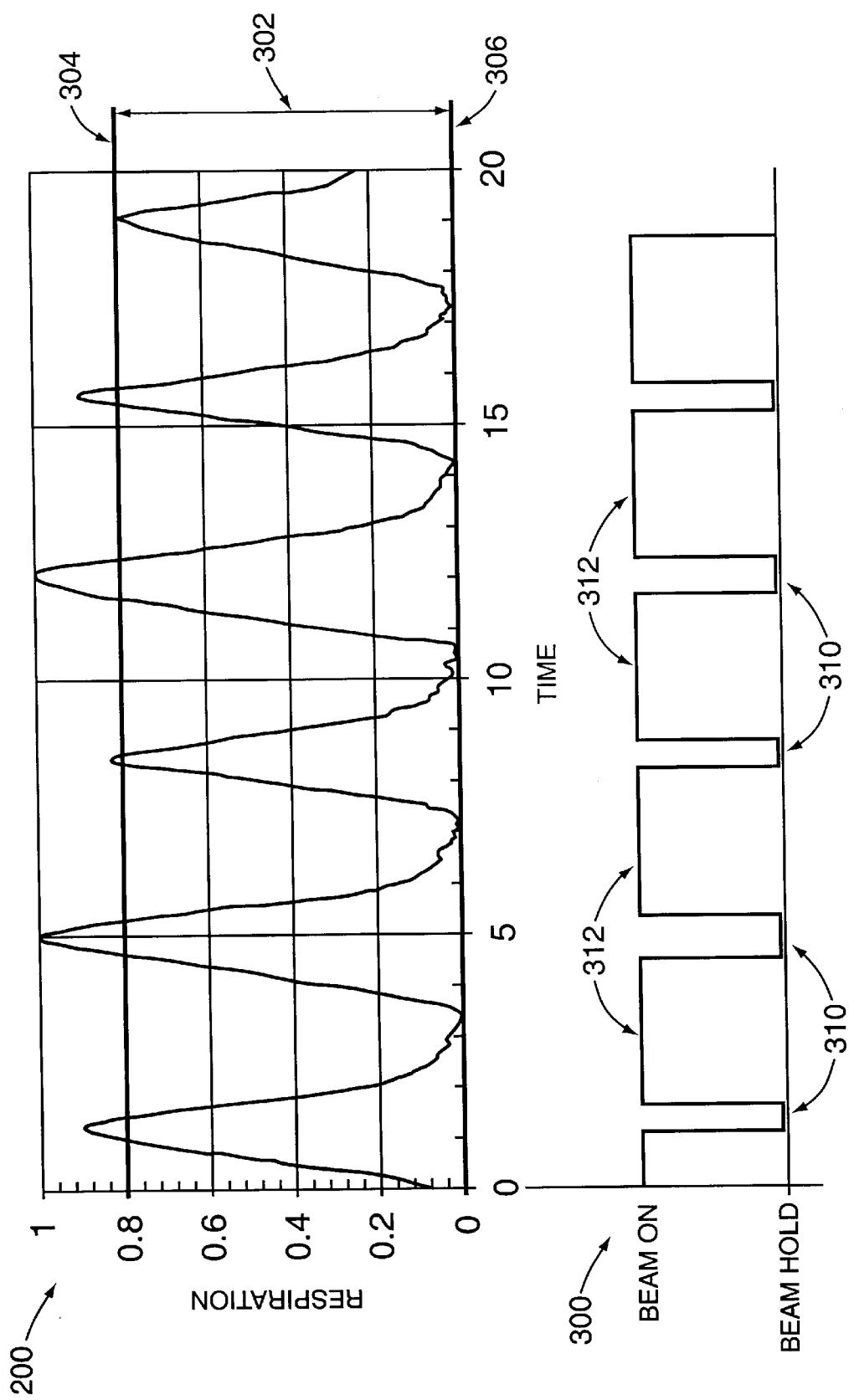
FIG. 3 depicts a motion signal chart and a gating signal chart.

Radiation is applied to the patient only when the motion signal is within the designated treatment intervals. Referring to FIG. 3, depicted are examples of treatment intervals, indicated by signal range 302, that has been defined over the motion data shown in motion signal chart 200. In the example of FIG. 3, any movement of the measured body location that exceeds the value of 0.8 (shown by upper boundary line 304) or which moves below the value of 0.0 (shown by lower boundary line 306) falls outside the boundaries of the treatment intervals.

Shown in FIG. 3 is an example of a gating signal chart 300 that is aligned with motion signal chart 200. Any motion signal that falls outside the treatment interval signal range 302 results in a "beam hold" gating signal threshold 310 that stops the application of radiation to the patient. Any motion signal that is within the treatment interval signal range 302 results in a "beam on" gating signal threshold 312 that allows radiation to be applied to the patient. In an embodiment, digital signals that represent the information shown in motion signal chart 200 are processed by computer 110 and compared to the threshold levels of the treatment interval signal range 302 to generate gating signal thresholds 310 and 312. Alternatively, gating signal thresholds 310 and 312 can be obtained by feeding analog motion signals to a comparator to be compared with analog threshold signals that correspond to treatment interval signal range 302. In any case, gating signal thresholds 310 and 312 are generated by computer 110 and are applied to the switch 116 that controls the operation of radiation beam source 102 (FIG. 1) to stop or start the application of a radiation beam at patient 106.

Figure 4:
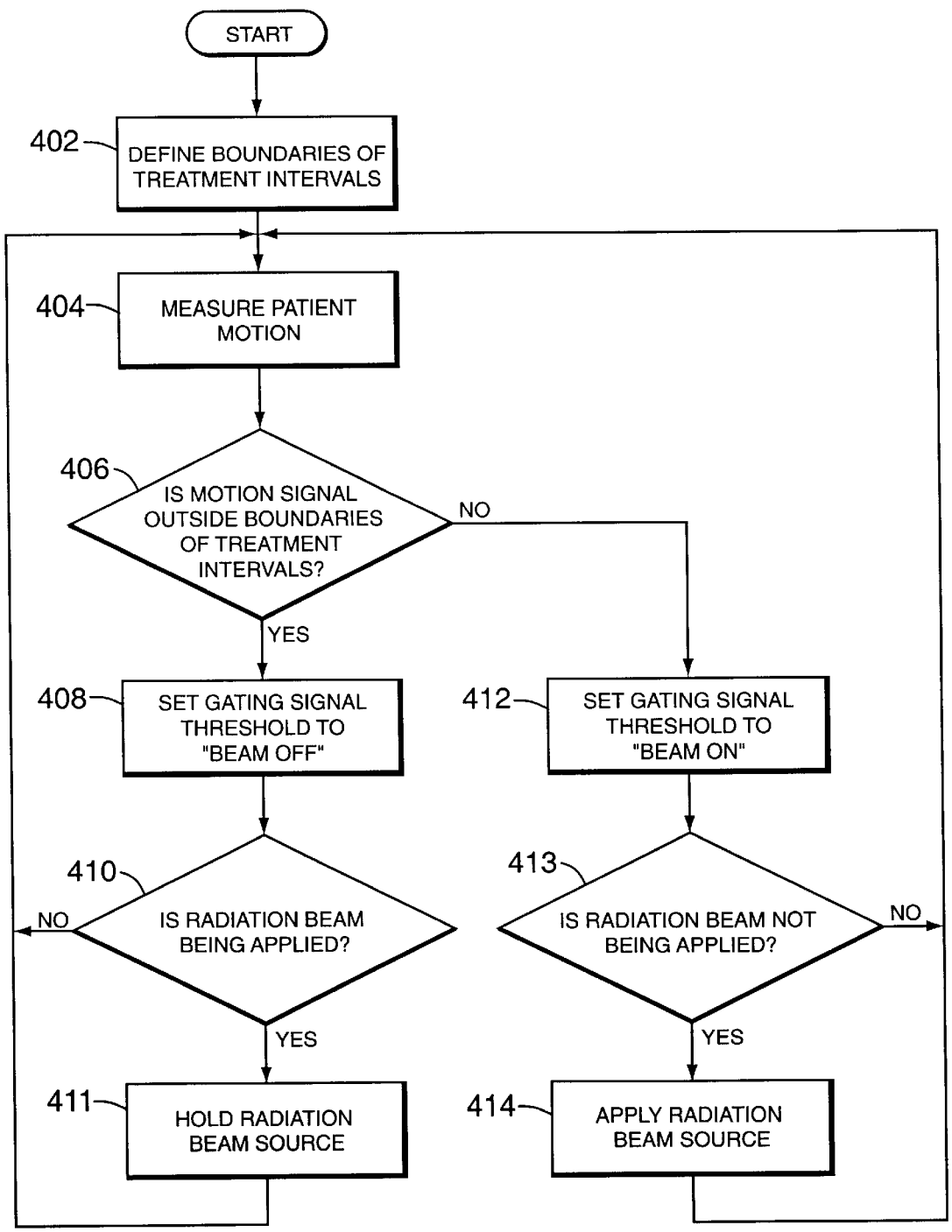
FIG. 4 is a flowchart showing process actions performed in an embodiment of the invention.

FIG. 4 is a flowchart of the process actions performed in an embodiment of the invention. The first process action is to define boundaries for the treatment intervals over the range of motion signals to be detected by a camera (402). As indicated above, any motion that fall outside the boundaries of the treatment intervals correspond to motion that is predicted to result in unacceptable levels of movement of the tumor or tissue targeted for irradiation. An optical or video imaging system, such as a video camera, is used to measure the physiological motion of the patient (404), and the output signals of the optical or video imaging system are processed to compare the measured motion signals with the threshold boundaries of the treatment intervals (406).

If the motion signal is outside the boundaries of the treatment intervals, then a "beam off" gating signal threshold is applied to a switch that is operatively coupled to the radiation beam source (408). If the radiation beam source is presently irradiating the patient (410), then the switch setting is operated to hold or stop the radiation beam (411). The process then returns back to process action 406.

If the motion signal is within the boundaries of the treatment intervals, then a "beam on" gating signal threshold is produced (412) and is applied to a switch that is operatively coupled to the radiation beam source. If the radiation beam source is presently not being applied to the patient (413), then the switch setting is operated to turn on or apply the radiation beam source to irradiate the patient (414). The process then returns back to process action 406.

According to one embodiment, the radiation beam source can be disengaged if a significant deviation is detected in the regular physiological movements of the patient. Such deviations can result from sudden movement or coughing by the patient. The position and/or orientation of the targeted tissue may unacceptably shift as a result of this deviation, even though the amplitude range of the motion signal still falls within the boundaries of the treatment intervals during this deviation. Thus, detection of such deviations helps define the appropriate time periods to gate the radiation treatment.

The present invention provides a method for detecting and predictively estimating a period of a physiological activity. In effect, the present invention can "phase lock" to the physiological movement of the patient. Since the gating system phase locks to the movement period, deviations from that period can be identified and appropriately addressed. For example, when gating to the respiratory cycle, sudden movement or coughing by the patient can result in deviation from the detected period of the respiration cycle. The radiation treatment can be gated during these deviations from the regular period. The present invention also provides a method for predictively estimating the period of the subsequent physiological movement to follow.

Figure 5:
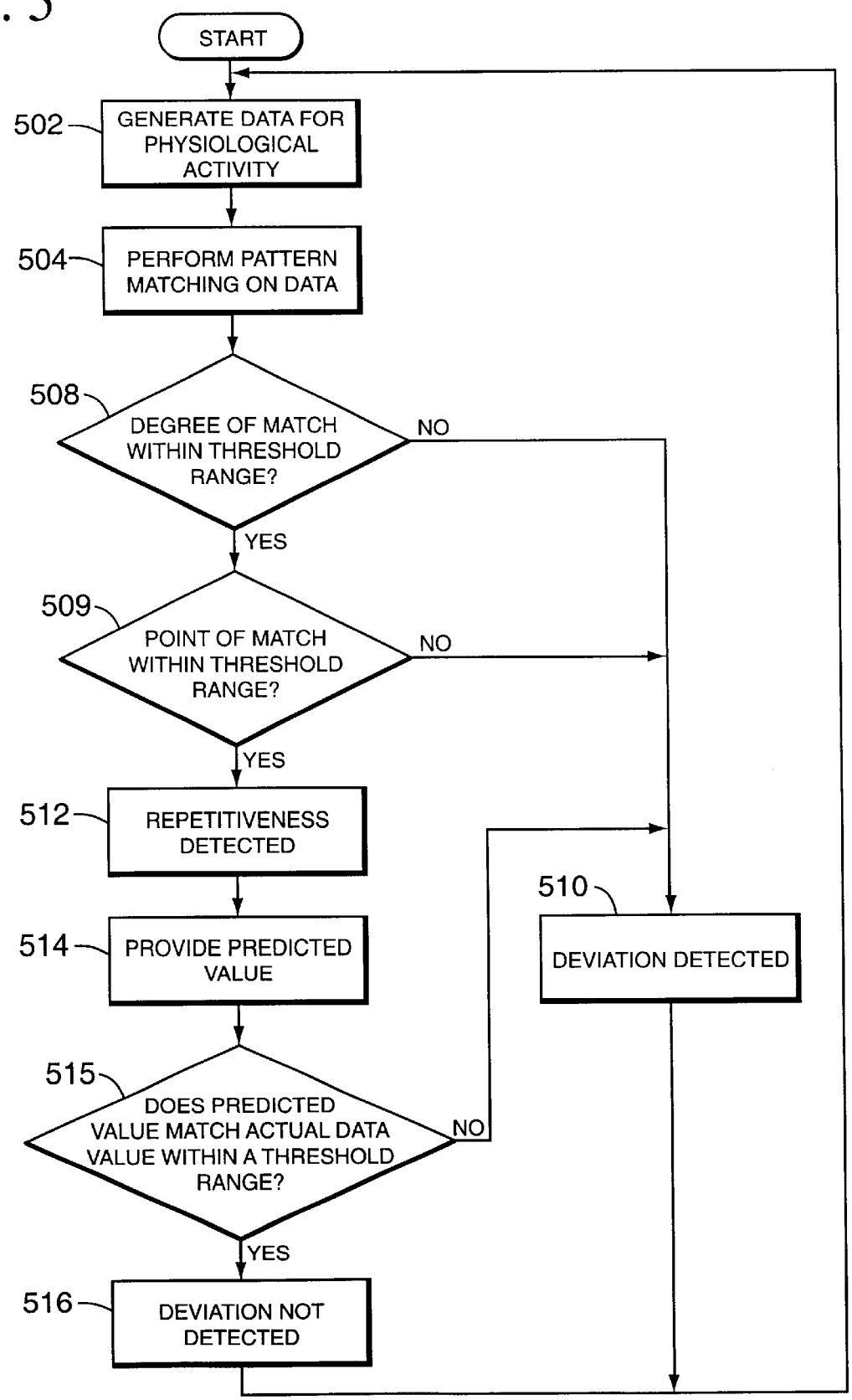
FIG. 5 is a flowchart showing process actions for detecting and predicting estimation of regular physiological movements.

FIG. 5 is a process flowchart of an embodiment of the invention to perform predictive estimation and detection of regular physiological movement cycles. In process action 502, an instrument or system (such as system 100 from FIG. 1) is employed to generate data signals representative of the physiological activity of interest. In an embodiment, the data signals comprises a stream of digital data samples that collectively form a signal wave pattern representative of the physiological movement under examination. A number of discrete measurement samples are taken for the physiological activity during a given time period. For example, in an embodiment of the invention directed towards respiratory measurement, approximately 200–210 data samples are measured for each approximately 7 second time interval.

In process action 504, pattern matching analysis is performed against the measured data samples. In an embodiment, the most recent set of data samples for the physiological signal is correlated against an immediately preceding set of data samples to determine the period and repetitiveness of the signal. An autocorrelation function can be employed to perform this pattern matching. For each new sample point of the physiological motion or physiological monitoring sensor signal, the process computes the autocorrelation function of the last n samples of the signal, where n corresponds to approximately 1.5 to 2 signal breathing periods. The secondary peak of the autocorrelation function is then identified to determine the period and repetitiveness of the signal.

In an alternate embodiment, an absolute difference function is used instead of an autocorrelation function. Instead of secondary peak, a secondary minimum in the absolute difference is searched for. For each new sample point of the physiological motion or physiological monitoring sensor signal, the process computes the minimum absolute difference between the two sets of data over a range of overlapping data samples. The secondary minimum corresponds to the data position that best matches the recent set of data samples with the preceding set of data samples.

Yet another alternate embodiment performs a pattern matching based upon a model the physiological activity being measured. The model is a dynamic representation of the physiological motion or physiological monitoring sensor signal for that physiological activity. The latest set of data samples is matched against the model to estimate parameters of the repetitive process.

Pattern matching using the measured physiological signal (504) provides information regarding the degree of match, as well as a location of best match for the repetitive process. If an autocorrelation function is employed in process action 504, then the relative strength of secondary peak provides a measure of how repetitive the signal is. A threshold range value is defined to provide indication of the degree of match between the two sets of data samples. If the strength of the secondary peak is within the defined threshold range (process action 508), then the degree of match indicates that the signal is repetitive, and the secondary peak location provides an estimate of the signal period. If an absolute difference function is used in process action 504, then the relative value of the secondary minimum provides a measure of how repetitive the signal is. If the value of the secondary minimum meets a defined threshold range (508), then the degree of match indicates that the signal is repetitive, and the secondary minimum location provides an estimate of the signal period.

If the correlation value of the secondary peak or secondary minimum does not meet the defined threshold range, then a deviation from the regular physiological activity is detected, thereby indicating an irregularity in the regular physiological movement of the patient (510). This irregularity could result, for example, from sudden movement or coughing of the patient. In an embodiment, this detected irregularity results in the generation of a "beam hold" signal that suspends the application of radiation at the patient.

If the degree of match indicates repetitiveness, the point of best match is tested to determine if the period is within a reasonable range. The location of the secondary peak or secondary minimum provides an estimate of the period of the physiological activity. In an embodiment, the point of best match is compared to a threshold range (509). If the point of best match does not fall within the threshold range, than a deviation from regular physiological activity is detected (510). If the point of best match falls within the threshold range, then the signal is accepted as being repetitive (512).

The estimate of the period based on the point of best match can be used to predict the period and waveform parameters of the next set of data samples for the signal (514). Note that process actions 504, 508, and 509 test for repetitiveness based upon a plurality of data samples over a range of such samples. However, in some circumstances, a significant deviation from normal physiological movement may actually occur within the new or most recent data sample(s) being analyzed, but because the overall set of data samples indicates repetitiveness (e.g., because of averaging of absolute differences over the range of data samples being compared), process actions 504, 508, and 509 may not detect the deviation. To perform a test for rapid deviation, the predicted value from process action 514 is compared with the next corresponding data sample (515). If the predicted value does not match the actual data sample value within a defined threshold range, then deviation is detected (510). If a comparison of the predicted and actual data sample values fall within the defined threshold range, then repetitiveness is confirmed, and deviation is not detected for that data sample range (516).

In an embodiment, the first time the process of FIG. 5 is performed, the pattern matching process action (504) is performed over the entire range of data samples. Thereafter, the pattern matching process action can be performed over a limited search interval, which is defined by the results of the prior immediate execution of the process. For example, the predicted value from process action 514 can be used to define the location of the search interval for the next set of data samples. However, if process action 508, 509, and 514 detect deviation based upon analysis of the initial search interval, then the search interval can be expanded to ensure that a deviation has actually occurred. The process of FIG. 5 can be repeated with the increased search interval to attempt to find a point of best match outside of the initial search interval. In an embodiment, this increased search interval comprises the entire range of data samples. Alternatively, the increased search interval comprises only an expanded portion of the entire range of data samples.

According to an embodiment of the invention, physiological gating can be performed based upon the phase of the physiological activity, rather than its amplitude. This is in contrast to the example shown in FIG. 3, in which the amplitude of the physiological movement signal defines the boundaries of the treatment intervals for the application of radiation.

Figure 9:
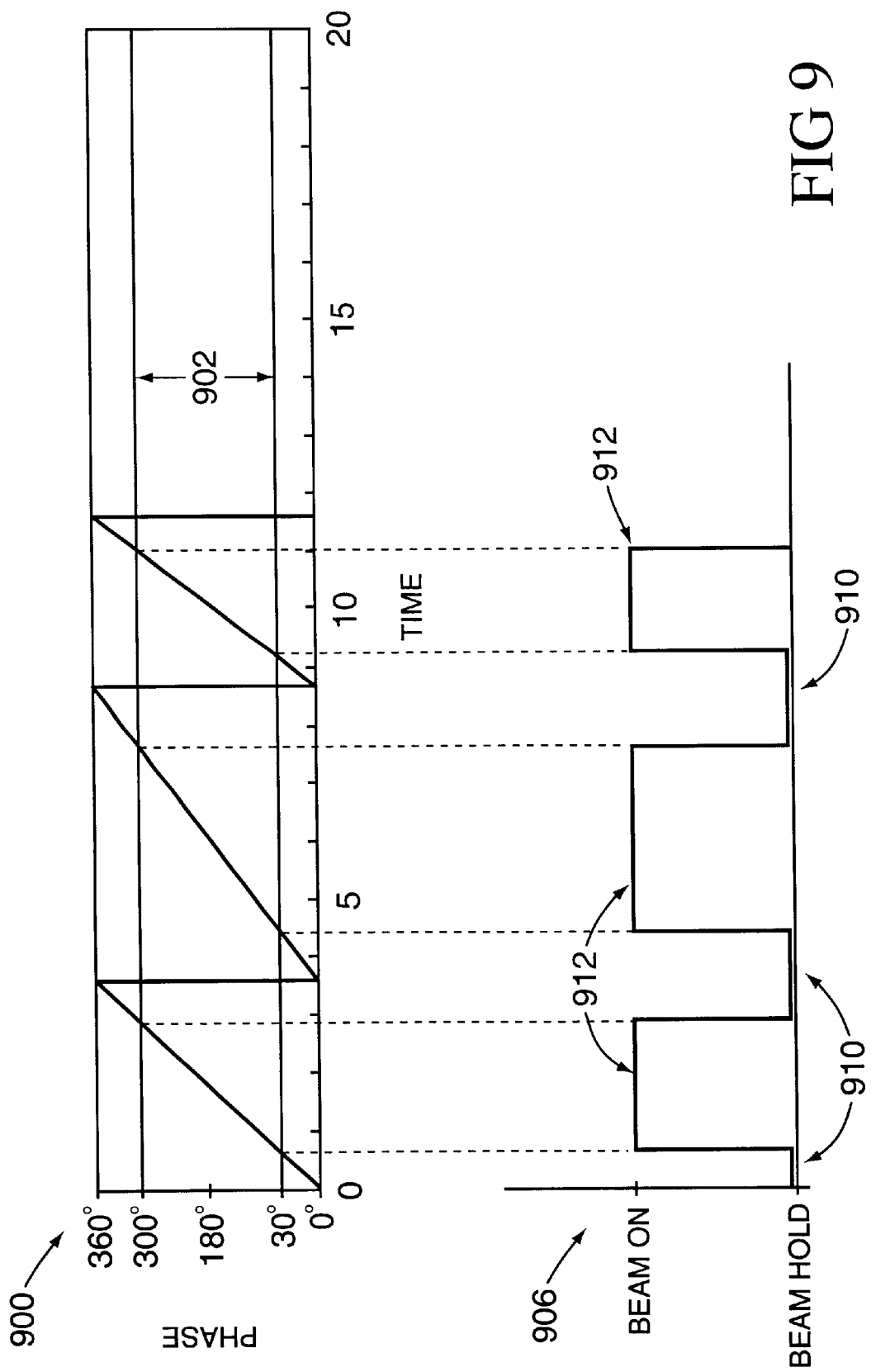
FIG. 9 depicts a phase chart synchronized with a gating signal chart.

Referring to FIG. 9, depicted is an example of a chart 900 showing the phase progression of a physiological movement signal. Treatment interval range 902 have been defined over the phase chart 900. In the example of FIG. 9, the boundaries of the treatment interval range 902 are defined by the phase of the detected signal. Radiation is applied to the patient only when the phase of the physiological movement signal falls within the boundaries of the treatment interval range 902. FIG. 9 depicts examples of treatment interval range 902 having boundaries that span from 30 degrees to 300 degrees. Thus, the applied radiation to the patient is suspended or stopped when the phase of the physiological movement signal is between 301 degrees to 29 degrees.

Shown in FIG. 9 is a gating signal chart 906 that is aligned with phase chart 900. A "beam hold" signal threshold 910 results if the phase of the physiological movement signal falls outside the treatment interval range 902. A "beam on" signal threshold 912 results if the phase of the physiological movement signal falls within the boundaries of the treatment interval range 902. The "beam on" and "beam hold" signal thresholds 910 and 912 are applied to a switch 116 that operatively controls the operation of a radiation beam source 102 (FIG. 1). If radiation is being applied to the patient, application of the "beam hold" signal threshold 910 triggers switch 116 to suspend or stop the application of radiation. If radiation to the patient is not being applied, application of the "beam on" signal threshold 912 triggers the application of radiation to the patient.

The predictive qualities of the present invention permits operation of a gating system even if the measured physiological movement involves motion that that is relatively fast when compared to the effectively operating speeds of gating system components. As just one example, consider a gating system that includes a switch for gating the radiation treatment, in which the switch requires a known time period Δt to fully engage. If the switching time period Δt is relatively slow compared to the measured physiological motion cycle, then a system employing such a switch in a reactive manner may not be able to effectively gate the application of radiation at the patient.

The present invention allows predictive triggering of switch 116 to compensate for the amount of time Δt required to fully engage the switch. A predicted period for a physiological activity can be obtained by employing the process of FIG. 5. A treatment interval range is defined over a portion of the period of the physiological activity. Based upon the time Δt required to fully actuate the switch 116, the switch 116 can be pre-actuated by this time period Δt prior to the time of the boundary of the treatment interval, so that the time for full actuation of the switch 116 coincides with the boundary of the treatment interval. Thus, the radiation can be effectively gated at the boundaries of the treatment interval, regardless of the operating speeds of the switch 116. The same procedure can also be employed to compensate for the operating speeds of other gating system components.

The following is an embodiment of the invention coded in the Visual Basic programming language. The following program code is directed to a process for detecting and predictively estimating the respiration cycle period using the absolute difference function:

```
Public Function Predict(ByVal i As Long, ByVal Range
    As Long, Period As Double,
MinAbsDiff As Double, Diff As Double) As Double
Dim j As Long, StartJ As Long, CurrJ As Long
Dim k As Long, MaxK As Long
Dim AbsDiff As Double
Dim NonnAbsDiff As Double, n As Long
k=Period–Range
MinAbsDiff 10000000#
StartJ=TimeRefldxBuf((i−201+Buflength) Mod
    BufLength)
CurrJ=TimeRefldxBuf((i−1+ButLength) Mod
    BufLength)
Do
   j=StartJ
   AbsDiff=0#
   n=0
   Do
     AbsDiff=AbsDiff+Abs(SigBuf(SigRefldxBuf(j))−
         SigBuf(SigRefldxBuf(j+k+ChartWidth) Mod
         ChartWidth)))
     n=n+1
     j=(j+10) Mod ChartWidth
   Loop While n<=(200−k)/10
   NormAbsDiff=100 * AbsDiff/(n * Abs(MaxSignal−
      MinSignal))
   If NormAbsDiff<=MinAbsDiff Then
     MinAbsDiff=NormAbsDiff
     MaxK=k
   End If
   k=k+1
Loop While k<=Period+Range
If MaxK>=40 And MaxK<=150 Then Period=MaxK
Predict=SigBuf(SigRefldxBuf(((CurrJ−Period+
   ChartWidth) Mod ChartWidth))
Diff=100 * Abs(SigBuf(SigRefldxBuf(CurrJ))−Predict)/
   Abs(MaxSignal−MinSignal)
If MinAbsDiff<=20 Then
   ProgressBar1.Value=MinAbsDiff
Else
   ProgressBar1.Value=20
End If
End Function
```

In this program code, the variable "i" represents a counter or index to the data sample being processed. The variable "Range" represents the search range that is to be analyzed. If the period of the physiological cycle has already been determined (i.e., from a prior execution of this program code), then the variable "Period" comprises the detected period. If the period has not yet been determined, then the variable "Period" is set to a default value representative of a normal respiration cycle (e.g., the number of data points in a normal breathing cycle, which is approximately 95 data samples in an embodiment of the invention where approximately 200–210 data samples are obtained over an approximately 7 second time period). The variable "MinAbsDiff" is the minimum absolute difference value over the search range. The variable "Diff" represents a comparison between the actual value of a next data sample and the expected value of that next data sample.

The variables "j", "StartJ", and "CurrJ" are counters or indexes into the data samples being processed. The variable "k" is a counter to the search range. The variable "MaxK" represents the position in the search range having the minimum absolute difference value. The variable "AbsDiff" maintains the sum of the absolute difference values for overlapping data samples. The variable "NormaAbsDiff" is the average absolute difference value for a particular position in the search range, which is represented as a percentage value. The variable "n" is used to track the position of the data samples relative to the search range which is represented as a percentage value. "Predict" is the predicted value that is returned by this program code.

The variable "MinAbsDiff" is initialized to a high value so that so that any subsequent absolute difference value will be smaller than the initialized value. In an embodiment, the set of data samples being processed comprises 200 data points. Thus, in this program code, the variable "StartJ" is initialized back 201 data samples. The variable "CurrJ" is initialized back one data sample. Because a circular array is being used, the "Buflength" variable is referenced during the initialization of both "StartJ" and "CurrJ".

The outer Do loop moves the current and preceding sets of data samples relative to each other. The outer Do loop is active while the variable "k" indicates that the program code is processing within the search range. In an embodiment, the search range is initially set at three positions to either side of a predicted position. The predicted position is based upon the period obtained for an immediately prior execution of the program code. If the program code has not been executed immediately prior, then a default period value is used. If an acceptable minimum absolute difference value is not found within this search range, then the search range can be expanded to, for example, 50 positions to either side of the predicted position.

The variable "j" is initialized to the "StartJ" value. The variables "AbsDiff" and "n" are also initialized prior to execution of the inner Do loop.

The inner Do loop performs the computation of the absolute difference values between the present set and prior set of data samples. The variable "AbsDiff" maintains the sum of the absolute difference of values for overlapping data samples being compared. Note that the number of data samples being analyzed to determine the absolute difference values varies based upon the position in the search range being processed. This results because different positions in the search range has different numbers of data samples that overlap with the previous set of data samples being compared. In the embodiment of this program code, the absolute difference function is computed using every $10^{th}$ signal sample point, i.e., a subsampled subtraction is used. Because a circular array is being used, the "Chartwidth" variable is referenced during the calculation of "AbsDiff".

The variables "MaxSignal" and "MinSignal" indicate a maximum and minimum range for signal values that have previously been sampled. These values can be established, for example, during a learning period for the system in which data samples are obtained for a plurality of respiratory cycles. The "NormAbsDiff" variable holds the average absolute difference value represented as a percentage value based upon the "MaxSignal" and "MinSignal" values.

If the "NormAbsDiff" value is less than or equal to a previously established "MinAbsDiff" value, then the "MinAbsDiff" variable is set to the "NormaAbsDiff" value. The "MaxK" variable is set to the value of "k" if the "MinAbsDiff" value is reset. The variable "k" is then incremented, and if the "k" value is still within the search range, then the program code returns back to the beginning of the outer Do loop.

The result of this program code is a candidate minimum absolute difference value and a candidate position for the minimum absolute difference. The MaxK value is compared to pre-defined threshold values to ensure that it falls within a correct range of values for the physiological activity being processed. Thus, in an embodiment, the MaxK value is tested to make sure that it is greater than or equal to 40 and less than or equal to 150. If the mark value meets the threshold range, then the variable "Period" is set to the "MaxK" value. The variable "Predict" returns the predicted value for the next set of data samples to be processed. The variable "Diff" indicates the difference value between the current data sample value and the predicted data sample value, and is represented as a percentage to the "MaxSignal" and "MixSignal" values.

In an embodiment, an image of a progress bar can be displayed to visually indicate the periodicity of the signal samples. According to the program code, if the "MinAbsDiff" value is less than or equal to a 20% difference, then the visual progress bar is updated with the computed "MinAbsDiff" value. Otherwise, the visual progress bar displays all other "MinAbsDiff" values that exceed a 20% difference as a default value of "20".

Figure 6A:
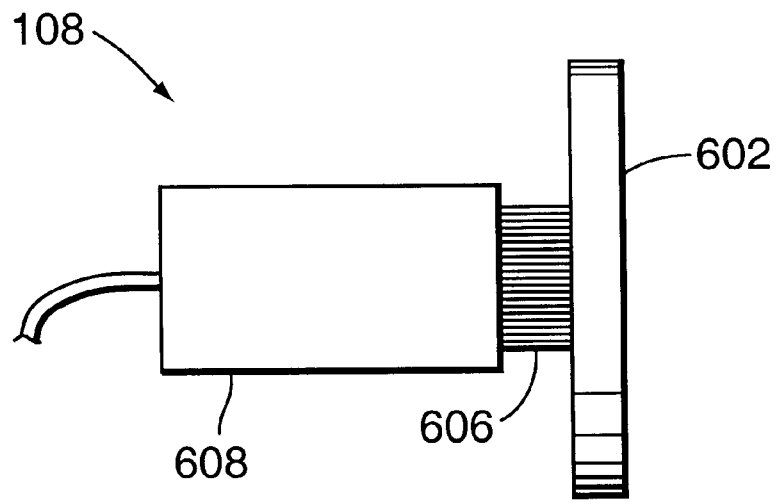
FIG. 6a depicts a side view an embodiment of a camera that can be utilized in the invention.
Figure 6B:
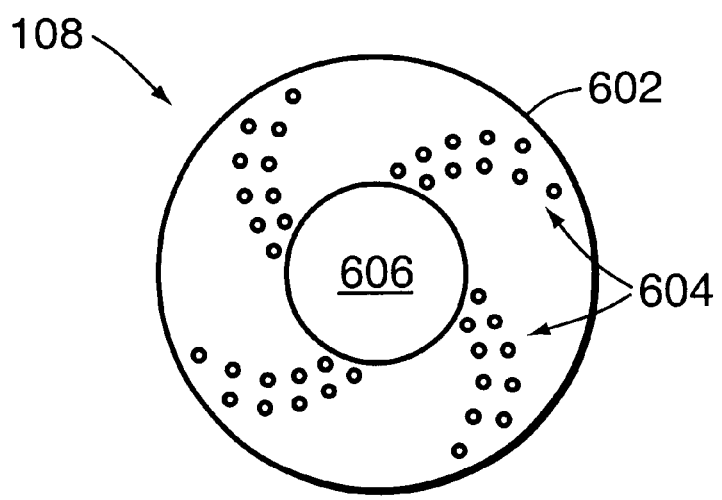

FIGS. 6a and 6b depict an embodiment of a camera 108 that can used in the present invention to optically or visually collect data representative of physiological movement. Camera 108 is a charge-couple device ("CCD") camera having one or more photoelectric cathodes and one or more CCD devices. A CCD device is a semiconductor device that can store charge in local areas, and upon appropriate control signals, transfers that charge to a readout point. When light photons from the scene to be images are focussed on the photoelectric cathodes, electrons are liberated in proportion to light intensity received at the camera. The electrons are captured in charge buckets located within the CCD device. The distribution of captured electrons in the charge buckets represents the image received at the camera. The CCD transfers these electrons to an analog-to-digital converter. The output of the analog-to-digital converter is sent to computer 410 to process the video image and to calculate the positions of the retro-reflective markers 406. According to an embodiment of the invention, camera 108 is a monochrome CCD camera having RS-170 output and 640×480 pixel resolution. Alternatively, camera 408 can comprise a CCD camera having CCIR output and 756×567 pixel resolution.

In a particular embodiment of the invention, an infra-red illuminator 602 ("IR illuminator") is co-located with camera 108. IR illuminator 602 produces one or more beams of infrared light that is directed in the same direction as camera 108. IR illuminator 602 comprises a surface that is ringed around the lens 606 of camera body 608. The surface of IR illuminator 602 contains a plurality of individual LED elements 604 for producing infrared light. The LED elements 604 are arranged in a spiral pattern on the IR illuminator 602. Infrared filters that may be part of the camera 108 are removed or disabled to increase the camera's sensitivity to infrared light.

According to an embodiment, digital video recordings of the patient in a session can be recorded via camera 108. The same camera 108 used for tracking patient movement can be used to record video images of the patient for future reference. A normal ambient light image sequence of the patient can be obtained in synchronization with the measured movement signals of markers 114.

FIGS. 7a and 7b depict an embodiment of a retro-reflective marker 700 that can be employed within the present invention. Retro-reflective marker 700 comprises a raised reflective surface 702 for reflecting light. Raised reflective surface 702 comprises a semi-spherical shape such that light can be reflected regardless of the input angle of the light source. A flat surface 704 surrounds the raised reflective surface 702. The underside of flat surface 704 provides a mounting area to attach retro-reflective marker 700 to particular locations on a patient's body. According to an embodiment, retro-reflective marker 700 is comprised of a retro-reflective material 3M#7610WS available from 3M Corporation. In an embodiment, marker 700 has a diameter of approximately 0.5 cm and a height of the highest point of raised reflective surface 702 of approximately 0.1 cm.

FIG. 8 depicts an apparatus 802 that can be employed to manufacture retro-reflective markers 700. Apparatus 802 comprises a base portion 804 having an elastic ring 806 affixed thereto. Elastic ring 806 is attached to bottom mold piece 808 having a bulge protruding from its center. A control lever 810 can be operated to move top portion 812 along support rods 814. Top portion 812 comprises a spring-loaded top mold piece 814. Top mold piece 814 is formed with a semi-spherical cavity on its underside. In operation, a piece of retro-reflective material is placed on bottom mold piece 808. Control lever 810 is operated to move top portion 812 towards base portion 804. The retro-reflective material is compressed and shaped between the bottom mold piece 808 and the top mold piece 814. The top mold piece 814 forms the upper exterior of the retro-reflective material into a semi-spherical shape.

In an alternate embodiment, marker 114 comprises a marker block having one or more reference locations on its surface. Each reference location on the marker block preferably comprises a retro-reflective or reflective material that is detectable by an optical imaging apparatus, such as camera 108.

Figure 11:
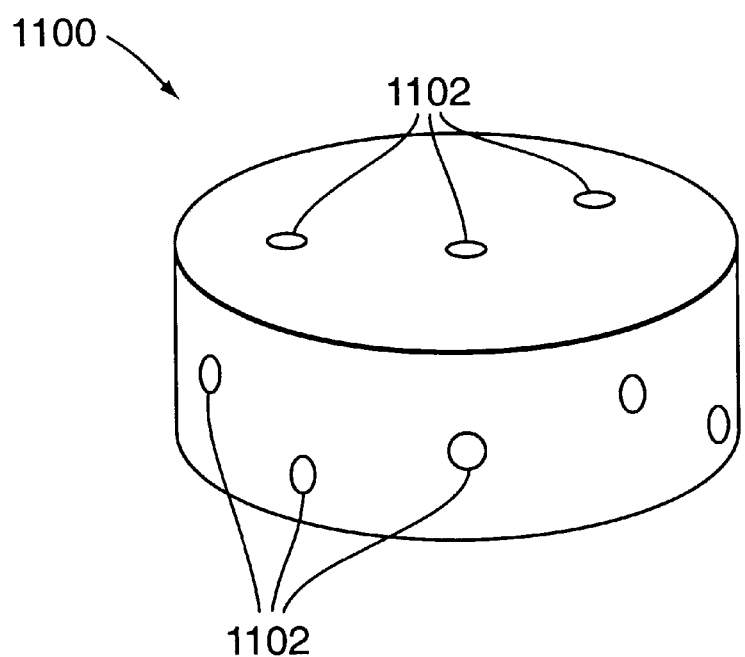
FIG. 11 depicts an embodiment of a hemispherical marker block.

FIG. 11 depicts an embodiment of a marker block 1100 having a cylindrical shape with multiple reference locations comprised of retro-reflective elements 1102 located on its surface. Marker block 1100 can be formed as a rigid block (e.g., from Styrofoam). Blocks made in this fashion can be reused a plurality of times, even with multiple patients. The retro-reflective elements 1102 can be formed from the same material used to construct retro-reflective markers 114 of FIGS. 7a and 7b. The marker block is preferably formed from a material that is light-weight enough not to interfere with normal breathing by the patient.

Figure 10:
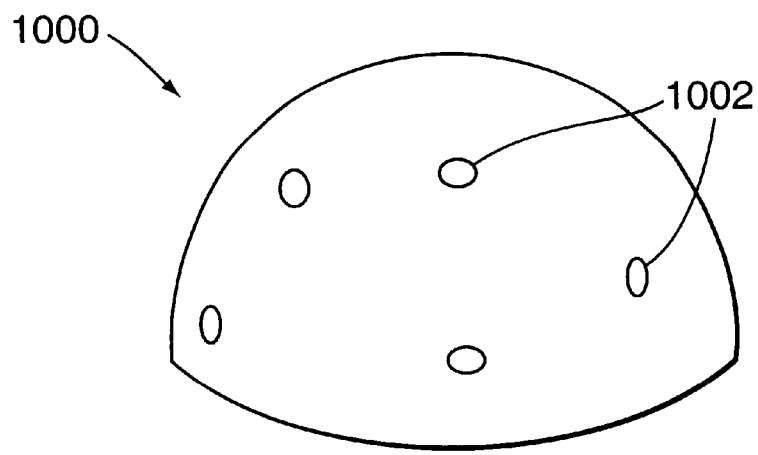
FIG. 10 depicts an embodiment of a cylindrical marker block.

A marker block can be formed into any shape or size, as long as the size, spacing, and positioning of the reference locations are configured such that a camera or other optical imaging apparatus can view and generate an image that accurately shows the positioning of the marker block. For example, FIG. 10 depicts an alternate marker block 1000 having a hemispherical shape comprised of a plurality of retro-reflective elements 1002 attached to its surface.

The marker block can be formed with shapes to fit particular body parts. For example, molds or casts that match to specific locations on the body can be employed as marker blocks. Marker blocks shaped to fit certain areas of the body facilitate the repeatable placement of the marker blocks at particular locations on the patient. Alternatively, the marker blocks can be formed to fit certain fixtures that are attached to a patient's body. For example, a marker block can be formed within indentations and grooves that allow it to be attached to eyeglasses. In yet another embodiment, the fixtures are formed with integral marker block(s) having reflective or retro-reflective markers on them.

An alternate embodiment of the marker block comprises only a single reference location/reflective element on its surface. This embodiment of the marker block is used in place of the retro-reflective marker 406 to detect particular locations on a patient's body with an optical imaging apparatus.

Further details regarding camera 108, markers 114, marker blocks, or procedures to optically measure physiological movements are described in copending U.S. patent application Ser. No. 09/178,384 (Varian Docket No. 98-34, Attorney Docket No. 236/223) and U.S. patent application Ser. No. 09/178,385 (Varian Docket No. 98-33, Attorney Docket No. 236/224), filed concurrently herewith, both of which are hereby incorporated by reference in their entirety.

Figure 12:
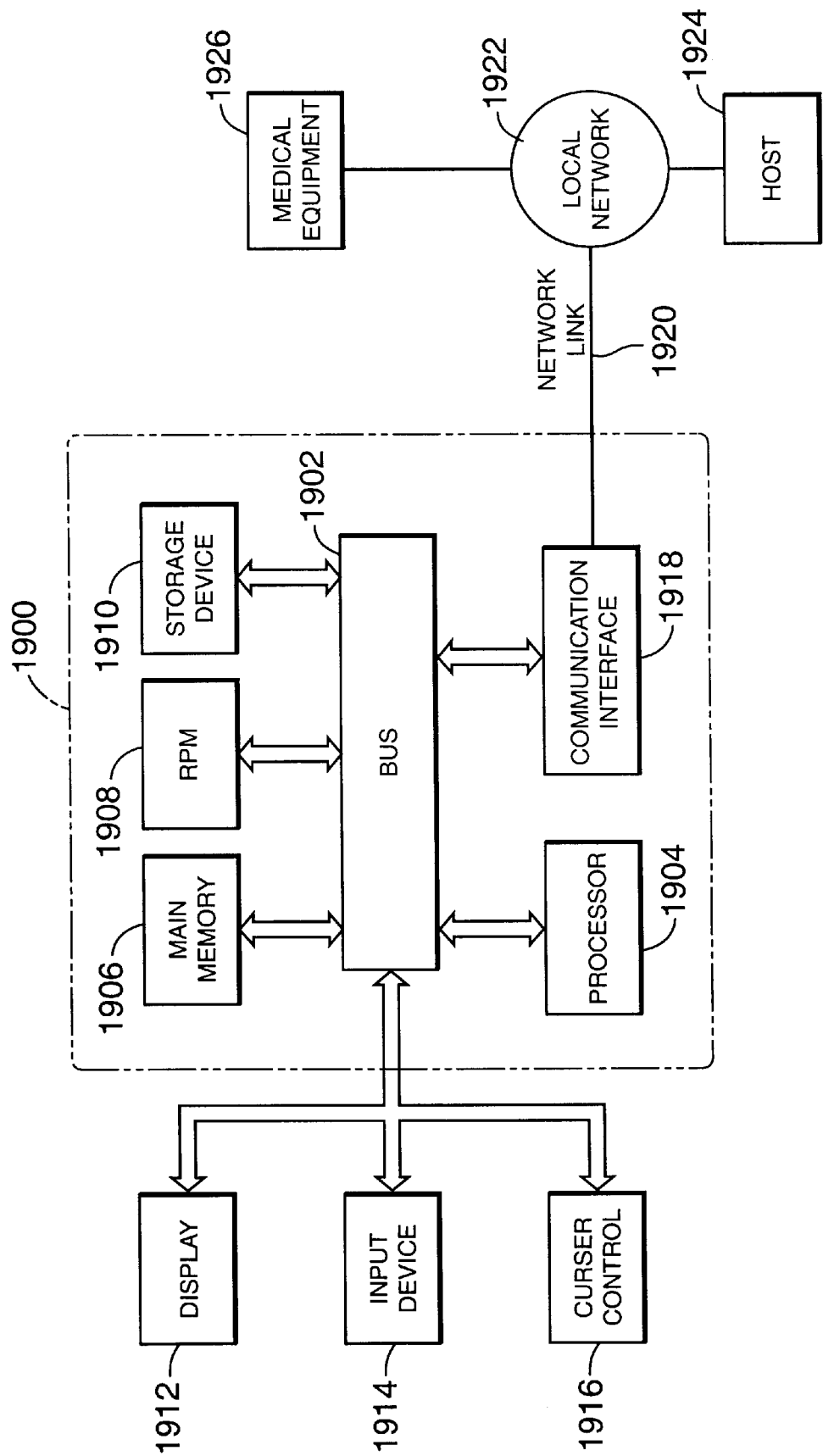
FIG. 12 is a diagram of a computer hardware system with which the present invention can be implemented.

FIG. 12 is a block diagram that illustrates an embodiment of a computer system 1900 upon which an embodiment of the invention may be implemented. Computer system 1900 includes a bus 1902 or other communication mechanism for communicating information, and a processor 1904 coupled with bus 1902 for processing information. Computer system 1900 also includes a main memory 1906, such as a random access memory (RAM) or other dynamic storage device, coupled to bus 1902 for storing information and instructions to be executed by processor 1904. Main memory 1906 also may be used for storing temporary variables or other intermediate information during execution of instructions to be executed by processor 1904. Computer system 1900 further includes a read only memory (ROM) 1908 or other static storage device coupled to bus 1902 for storing static information and instructions for processor 1904. A data storage device 1910, such as a magnetic disk or optical disk, is provided and coupled to bus 1902 for storing information and instructions.

Computer system 1900 may be coupled via bus 1902 to a display 1912, such as a cathode ray tube (CRT), for displaying information to a user. An input device 1914, including alphanumeric and other keys, is coupled to bus 1902 for communicating information and command selections to processor 1904. Another type of user input device is cursor control 1916, such as a mouse, a trackball, or cursor direction keys for communicating direction information and command selections to processor 1904 and for controlling cursor movement on display 1912. This input device typically has two degrees of freedom in two axes, a first axis (e.g., x) and a second axis (e.g., y), that allows the device to specify positions in a plane.

The invention is related to the use of computer system 1900 for detecting and predictively estimating physiological cycles. According to one embodiment of the invention, such use is provided by computer system 1900 in response to processor 1904 executing one or more sequences of one or more instructions contained in main memory 1906. Such instructions may be read into main memory 1906 from another computer-readable medium, such as storage device 1910. Execution of the sequences of instructions contained in main memory 1906 causes processor 1904 to perform the process steps described herein. One or more processors in a multi-processing arrangement may also be employed to execute the sequences of instructions contained in main memory 1906. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 1904 for execution. Such a medium may take many forms, including but not limited to, non-volatile media, volatile media, and transmission media. Non-volatile media includes, for example, optical or magnetic disks, such as storage device 1910. Volatile media includes dynamic memory, such as main memory 1906. Transmission media includes coaxial cables, copper wire and fiber optics, including the wires that comprise bus 1902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1904 for execution. For example, the instructions may initially be carried on a magnetic disk of a remote computer. The remote computer can load the instructions into its dynamic memory and send the instructions over a telephone line using a modem. A modem local to computer system 1900 can receive the data on the telephone line and use an infrared transmitter to convert the data to an infrared signal. An infrared detector coupled to bus 1902 can receive the data carried in the infrared signal and place the data on bus 1902. Bus 1902 carries the data to main memory 1906, from which processor 1904 retrieves and executes the instructions. The instructions received by main memory 1906 may optionally be stored on storage device 1910 either before or after execution by processor 1904.

Computer system 1900 also includes a communication interface 1918 coupled to bus 1902. Communication interface 1918 provides a two-way data communication coupling to a network link 1920 that is connected to a local network 1922. For example, communication interface 1918 may be an integrated services digital network (ISDN) card or a modem to provide a data communication connection to a corresponding type of telephone line. As another example, communication interface 1918 may be a local area network (LAN) card to provide a data communication connection to a compatible LAN. Wireless links may also be implemented. In any such implementation, communication interface 1918 sends and receives electrical, electromagnetic or optical signals that carry data streams representing various types of information.

Network link 1920 typically provides data communication through one or more networks to other devices. For example, network link 1920 may provide a connection through local network 1922 to a host computer 1924 or to medical equipment 1926 such as a radiation beam source or a switch operatively coupled to a radiation beam source. The data streams transported over network link 1920 can comprise electrical, electromagnetic or optical signals. The signals through the various networks and the signals on network link 1920 and through communication interface 1918, which carry data to and from computer system 1900, are exemplary forms of carrier waves transporting the information. Computer system 1900 can send messages and receive data, including program code, through the network(s), network link 1920 and communication interface 1918.

In the foregoing specification, the invention has been described with reference to specific embodiments thereof. It will, however, be evident that various modifications and changes may be made thereto without departing from the broader spirit and scope of the invention. For example, the operations performed by computer 110 can be performed by any combination of hardware and software within the scope of the invention, and should not be limited to particular embodiments comprising just a particular definition of "computer". The specification and drawings are, accordingly, to be regarded in an illustrative rather than restrictive sense.

What is claimed is:

1. A method of gating the application of therapeutic radiation comprising:
   measuring a first set of signal data representative of a physiological movement of a patient during a first time period;
   pattern matching the first set of signal data with a second set of signal data related to measured physiological movement of a patient during a second time period to identify degree of deviation from periodicity of the physiological movement; and
   gating therapeutic radiation to the patient if the degree of deviation from periodicity exceeds a threshold.

2. The method of claim 1 in which the first set of signal data and the second set of signal data are pattern matched using an autocorrelation function.

3. The method of claim 1 in which the first set of signal data and the second set of signal data are pattern matched using an absolute difference function.

4. The method of claim 1 further comprising:
   determining a degree of match between the first set of signal data and the second set of signal data.

5. The method of claim 4 in which the degree of match is determined by a secondary peak value of an autocorrelation function.

6. The method of claim 4 in which the degree of match is determined by a secondary minimum value of an absolute difference function.

7. The method of claim 4 further comprising:
   comparing the degree of match to a threshold range.

8. The method of claim 7 in which the degree of match outside the threshold range indicates deviation from a normal physiological movement.

9. The method of claim 7 in which the degree of match within the threshold range indicates a repetitive physiological movement.

10. The method of claim 9 in which a point of best match indicates a period of the physiological movement.

11. The method of claim 1 further comprising:
    predicting a period of the physiological movement during a third time period.

12. The method of claim 11 further comprising:
    predictively actuating a gating system component based upon the predicted period.

13. The method of claim 1 further comprising:
    determining a period of the physiological movement.

14. The method of claim 13 further comprising:
    defining a treatment interval to apply the therapeutic radiation to a patient.

15. The method of claim 14 in which the treatment interval is defined by phase of the physiological movement.

16. The method of claim 1 in which the second set of signal data is a data model of the physiological movement of the patient.

17. A method of gating the application of radiation, comprising:
    measuring signal data representative of at least a portion of a physiological movement to form a set of ordered measurement samples;
    pattern matching the set of ordered measurement samples against prior measurement samples of the physiological movement to determine deviation from periodicity of the set of ordered measurement samples; and
    gating therapeutic radiation to the patient if the deviation from periodicity is outside a threshold range.

18. The method of claim 17 in which the second set of ordered measurement samples overlaps with the prior measurement samples.

19. The method of claim 17 in which the physiological movement comprises breathing movement.

20. The method of claim 17 in which pattern matching is performed using an autocorrelation function.

21. The method of claim 17 in which pattern matching is performed using an absolute difference function.

22. The method of claim 17 further comprising;
    defining a treatment interval to apply radiation to a patient.

23. The method of claim 22 in which the treatment interval is defined based upon phase of the physiological movement.

24. The method of claim 17 further comprising:
    determining a predicted value for an additional measurement sample for the physiological movement.

25. The method of claim 24 in which radiation gating occurs if the predicted value deviates from the additional measurement sample beyond a designated threshold level.

26. The method of claim 17 in which the step of pattern matching comprises shifting the set of ordered measurement samples against the prior measurement samples at a plurality of offset sample positions to determine position of best match.

27. The method of claim 26 in which an absolute difference function is used to determine the position of best match.

28. The method of claim 26 in which a search range for position of best match is established based upon a predicted position, in which the predicted position is based upon a period established from the prior measurement samples.

* * * * *